United States Patent [19]

Alvarez Cambras

[11] Patent Number: 4,624,249
[45] Date of Patent: Nov. 25, 1986

[54] ORTHOPEDIC EXTERNAL FIXING APPARATUS

[75] Inventor: Rodrigo J. Alvarez Cambras, Havana, Cuba

[73] Assignee: Medicuba, Havana, Cuba

[21] Appl. No.: 697,849

[22] Filed: Feb. 4, 1985

[30] Foreign Application Priority Data

Dec. 4, 1984 [CU] Cuba ........................................ 36222

[51] Int. Cl.⁴ .............................................. A61F 5/04
[52] U.S. Cl. ............................... 128/92 ZK; 128/92 R
[58] Field of Search ................. 128/92 A, 92 R, 92 H

[56] References Cited

U.S. PATENT DOCUMENTS

| | | | |
|---|---|---|---|
| 1,789,060 | 1/1931 | Weisenbach | 128/92 A |
| 4,127,119 | 11/1978 | Kronner | 128/92 A |
| 4,308,863 | 1/1982 | Fischer | 128/92 A |
| 4,363,624 | 12/1982 | Jaquet | 128/92 A |
| 4,475,546 | 10/1984 | Patton | 128/92 A |

*Primary Examiner*—Gene Mancene
*Assistant Examiner*—C. W. Shedd
*Attorney, Agent, or Firm*—Lackenbach Siegel Marzullo Presta & Aronson

[57] ABSTRACT

An external fixator having specialized pin holders which are slidably, but fixably disposed within hollow spacing members of the external fixation frame. The spacing members are externally threaded to receive nuts which fix the pin holders and the members are slotted to receive transfixion pins which are fixed in the pin holders by means of set screws.

4 Claims, 5 Drawing Figures

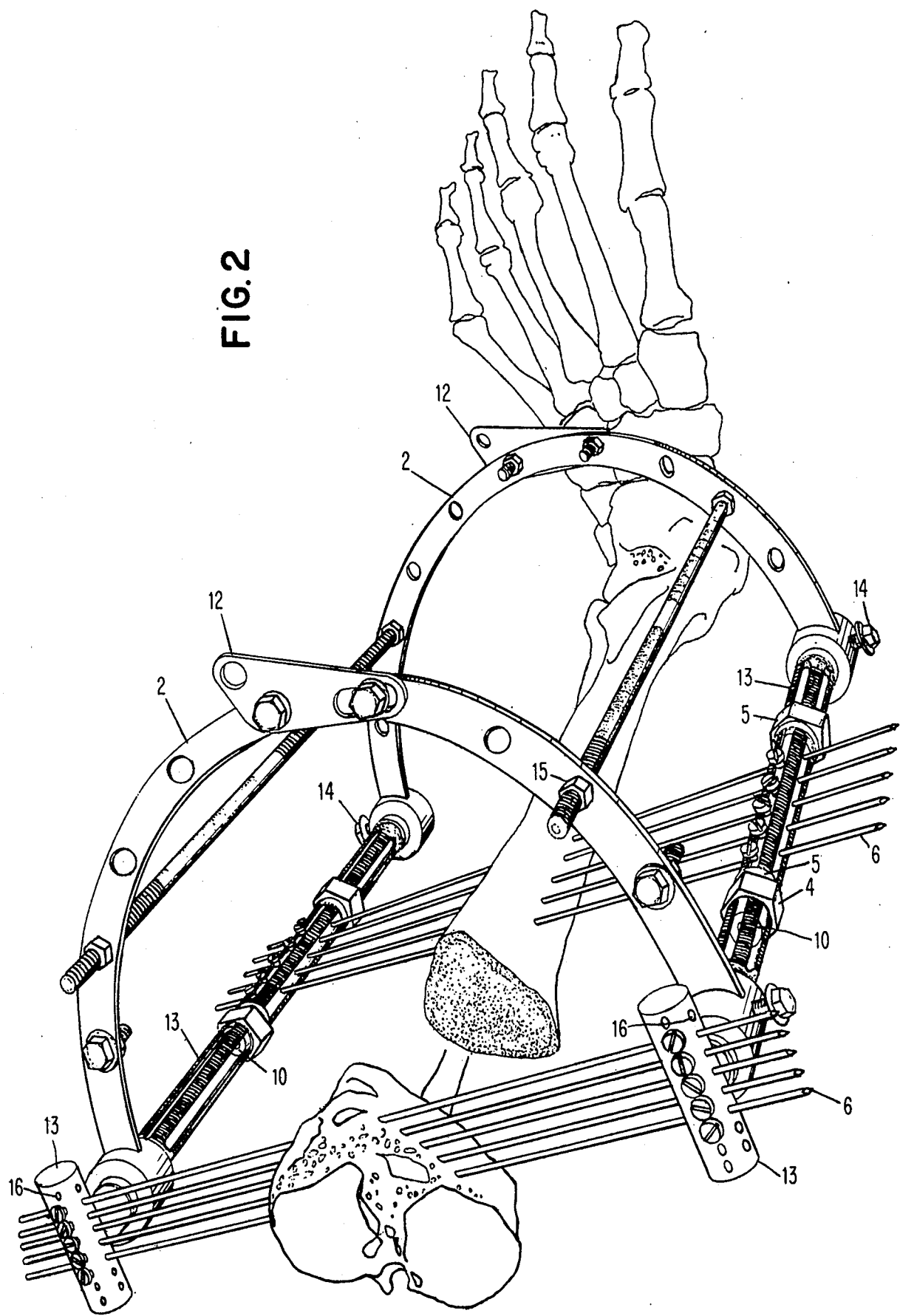

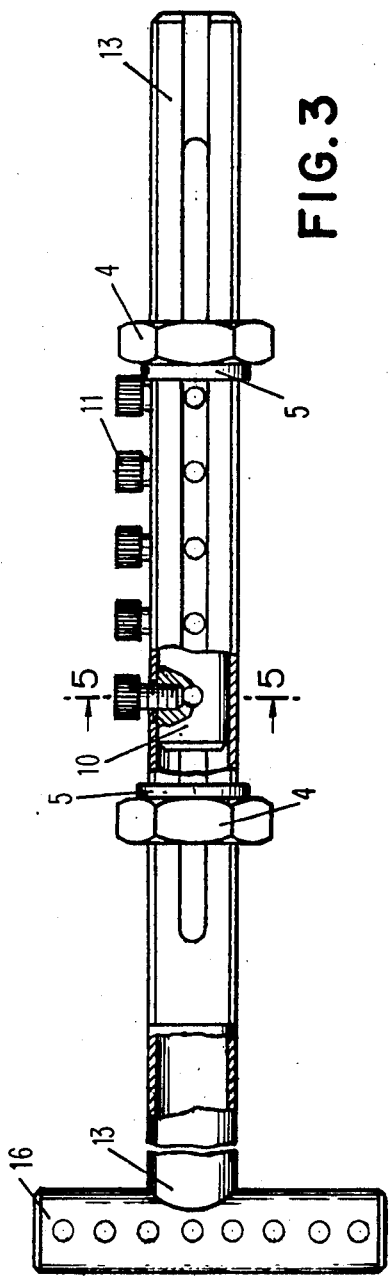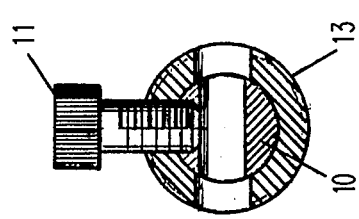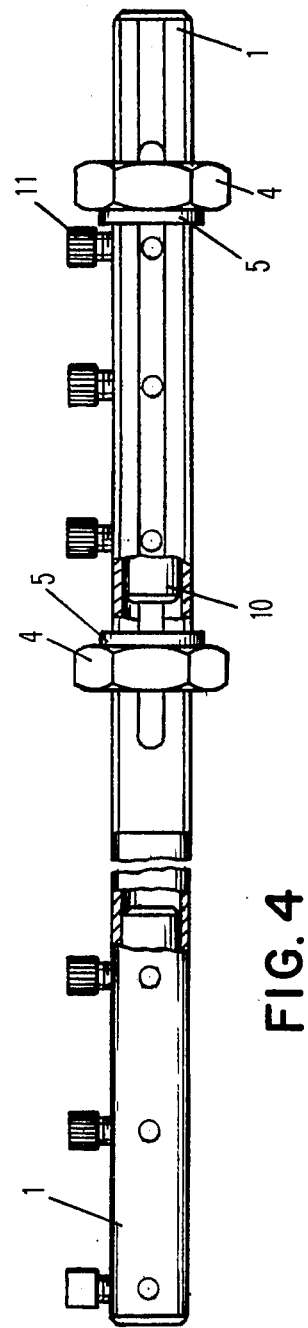

ORTHOPEDIC EXTERNAL FIXING APPARATUS

This invention is related to health and specially to of orthopaedics and traumatology.

BACKGROUND OF THE INVENTION

Many propositions have been advanced regarding orthopaedic external fixator devices, which comprise basically the adjustable mounting of assembly mechanisms connecting different parts of a fractured bone and permitting its management and setting in the desired position.

As an example of these orthopaedic external fixator devices we can mention Soviet Pat. No. 227511, with international classification A61B 17/18, which favours an orthopaedic external fixator composed of five half-rings joined in pairs by slotted small plates to which there are fixed transfixion wires going over the bone in a lineal form within the same plane on both sides of the fracture's core. The system already formed has a mechanism of screws which allows the fracture to be tractional or compressed when being actioning actional over the hoops.

Soviet Pat. No. 827049, international classification A61B 17/18, favours an orthopaedic external fixator composed of four half-rings held within their elements to pass the transfixion wires, which can move together in the plane supporting them every time the mechanism of screws that join the half-rings by pairs is rotated one.

The Czechoslovakian Pat. No. 503050, international classification A61B 17/18, favours an orthopaedic external fixator composed of half-rings containing in their ends elements carrying transfixion wires and screws which also serve to fit and join the half-rings. When actioned they permit their separation or reciprocal shortening together with the wires transfixing the bone on both sides of the fracture core.

As the nearest prototypes we have the orthopaedic external fixator favored by the Soviet Pat. No. 227511, international classification A61B 17/18, which is composed of four half-rings joined by pairs with slotted small plates containing elements coupled to them with transfixion wires crossing lineally over the bone in a common plane. It also includes an actioning mechanism placed conveniently between the inner half-rings, which allows the traction or compression of the bone.

The Soviet Pat. No. 910153, international classification A61B 17/18, favours an orthopaedic external fixator formed by two rings with joint rods between them having transfixion wires crossed in parallel planes to fix the bone. A dispositive serving as a support to hold the patient's limb and the orthopaedic external fixator during surgery is also shown. Soviet Pat. No. 227511 presents technical imperfections such as: (1) having to mobilize the whole fixator structure during the operation of traction or compression of a fracture makes the fixator a little bit unstable; (2) the slotted small plate containing the elements that fix the transixion wires on their ends brings less rigidity to the system and this could damage the pathological bone.

The mechanisms for moving the ring parallel during traction or compression of a fracture is very complex since it contains many elements.

Regarding the Soviet Pat. No. 827049, the external fixator device has the technical disadvantage of having a transfixion point per each ring, so when its wire in connection with the bone is loosened, the apparatus will easily displace laterally, thus acting against the bone consolidation process.

The Czechoslovakian Pat. No. 593050 presents the same technical difficulty since the action of traction or compression of a fracture with this system implies that all rings together have to be moved, thus bringing less stability to the unit.

Concerning Soviet Pat. No. 910153, the fixator has the technical disadvantage of having the wires transfixing the bone crossing in a common plane, thus making the fixator lose mechanical qualities in that zone. The rings bring ambulatory discomfort to the patient. A special support table is essential for its location during the surgical process. It is also necessary to guarantee the ring parallelism during the process of compression or traction in order not to create power components that would deviate it from its course.

The objectives of the invention are: (a) the creation of an external fixator device whose simplicity could make the labor of the specialist easier during surgery and its later follow-up; (b) to make possible that it can be used with satisfactory results in: compression, traction, epiphysial and diaphysial fractures, stabilization, arthrodesis, pseudoarthrosis, etc.

SUMMARY OF THE INVENTION

The innovation consists in that this fixator is composed of two bars joined by a half-ring fitted to the two bars, through fixing screws which are joined together by rods and nuts so as to achieve a more stable system. The bars have a solid section and another one in a tubular form, through which there can pass pistons or pin holders, containing drills for this purpose, as well as the transfixion wires aligned for this in a plane normal to the symmetrical one of the device, the wires are fixed by screws. Moreover, when it is required by the pathology, on the end of the tubular bars a carrier, where transfixion wires are fixed by screws, is adjusted. Adjustable according to certain pathologies, the apparatus is composed of tubular bars with a solid "T" shaped end containing drilled holes movable in a plane normal to the symmetrical one of the device, perpendicular to the shaft of the bars, and having transfixion wires. These apparatus are threaded along the whole tubular zone of the external surface and have slots with a space between them enabling the axial slipping of the bars of the transfixion wires contained in the pistons, or pin holders, as well as of the fixing screws when the fitting nuts joined at this part of the bars are actioned. The fixators also have lugs that when assembled adequately in its structure allow fracture reduction.

Representative figures are as follows:

FIG. 2 is an isometric view of the orthopaedic external fixator with "T" shaped bars.

FIGS. 3–5 are clarifying views of the instant device.

Figure 1:
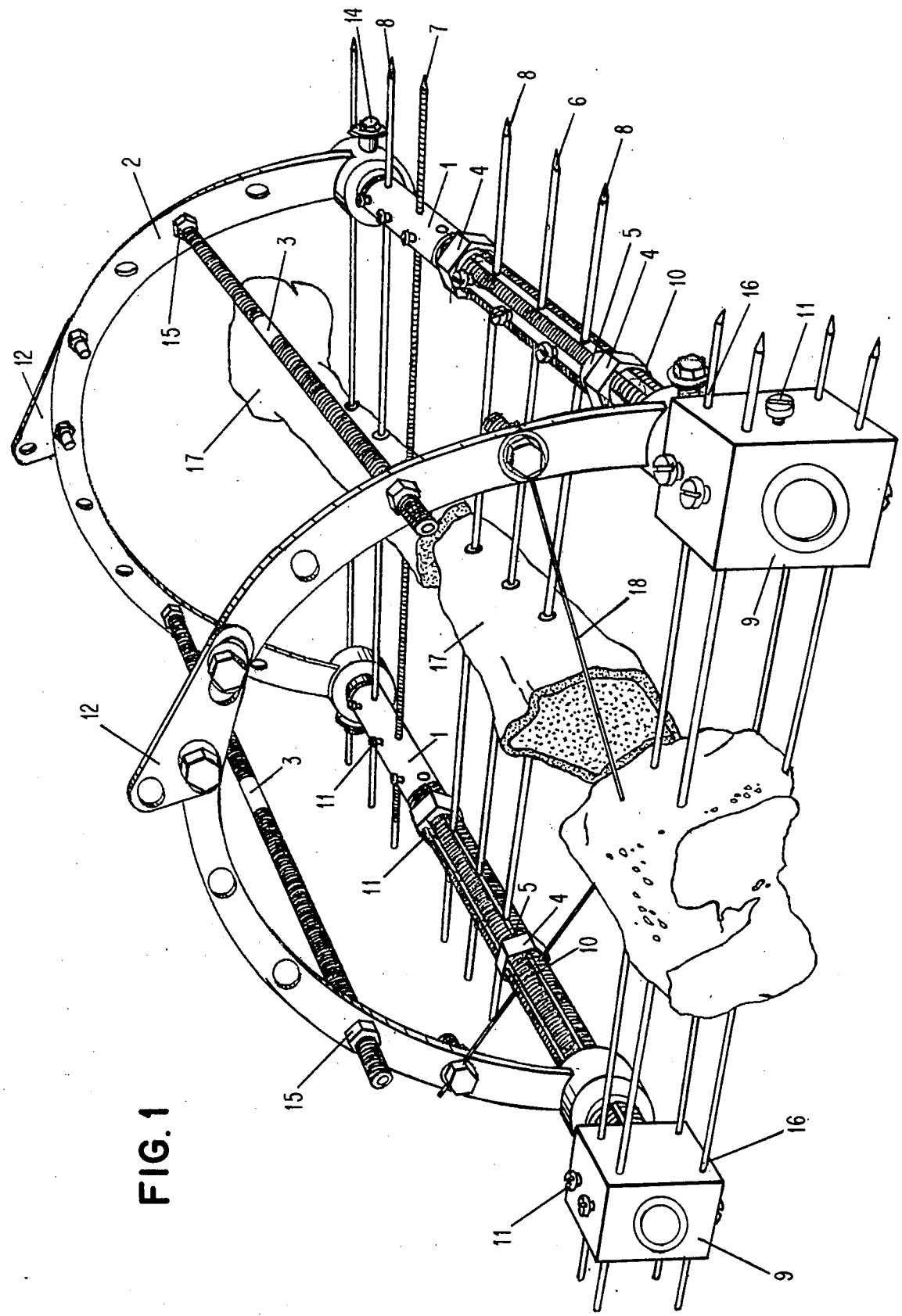
FIG. 1 is an isometric view of the orthopaedic external fixator and its carrier dispositive.

DETAILED DESCRIPTION OF THE PREFERRED EMBODIMENTS (FIG. 1) this device is used to carry bone fragments. It consists of two bars 1 joined by two half-rings 2 linked together by two rods 3, thus forming a rigid space structure. Bars 1 have one solid section and one slotted tubular section. They have a right parallelpiped adusted on the tubular end 9 while is designated as a bone carrier. Through the inner part of the tubular section slip pistons or pin holders, 10 with drilled holes 16 through which transfixion wires 6 are passed. In the external part of this zone are nuts and washers 5 for the adjustment of the pistons 10. In the solid section are drilled holes 16 aligned in a normal direction to the symmetrical plane of the device to hold smooth transfixion wires 6 with thread 7 or with a stop 8 and screws used to fix them. Also, when it is required, we use special lugs 12 which will serve to reduce bone fractures. This orthopaedic external fixator device works as follows: if a portion of the tibia bone 17 is going to be resected (cut in blocks) without diminishing its length, then the fixator is placed on the affected limb portion in such a way that the bars 1 keep laterally aligned through the bone (the zone to be resected being taken as the device location reference). The solid portion of the bars 1 is placed on the distal part and the bone carrier 9 on the proximal one. The transfixion wires 6 are passed through the drilled holes 16 located in the solid zone of the bars 1 and also through the carrier 9, fixing them with the screws 11 of the bars 1 and the carrier 9. The pistons are moved into the proximal portion of the tibia along the slots of the bars 1 with the fitting nuts 4, with the pistons 10 kept at a higher level compared with the bone portion 17 to be resected. Transfixion wires 16 are passed through the pistons 10 with the proximal part of the tibia 17 being fixed by the screws 11. The nuts 4 are kept under manipulation until the washers 5 meet with the wires 6. The distal part of the bone portion is resected beginning the migration of the bone part 17 which is controlled by the wires 6 carrying the pistons 10 at an adequate speed until this fragment meets with the bone part 17 supported by the wires 6 in the solid portion of the bars 1 until its consolidation. In order to prevent the device from lateral displacement, transfixion wires with threads 7 with stop 8 and a stabilizer are added to it.

Orthopaedic external fixator device. (FIG. 2)

This device is used to make an elongation, an epiphysial traction or an epiphysial corticotomy of limbs by operation of one single unit. It consists of two bars 13 joined by two half-rings 2 which together are linked by two rods 3 threaded to their ends, fixing the half-rings 2 with nuts and lock-nuts 15 thus forming a rigid space structure that will serve as an effective support for the bone in a lengthening process.

The bars 13 have a tubular portion with three slots with a 90° space between them, threaded in the external zone along this portion. On one end, they have a "T" shaped solid portion where one of the half-rings 2 is adjusted. In this solid part, perpendicular to the tubular section and normal in respect to the symmetrical plane of the apparatus, there are drilled holes 16, through which transfixion wires 6 pass and, perpendicular to these there are screws 11 for their fixation.

Along the internal tubular part of the bars 15 there will slip pistons 10 with drilled holes 16 permitting the passing of transfixion wires 16 trimmed in a normal plane normal to the symmetrical plane of the apparatus and also with fixation screws 11. This orthopaedic external fixator device functions as follows: In an elongation the solid portion of the bars 13 is aligned in such a way that the transfixion wires 6 in this part may laterally go through the distal portion of the tibial plateau and parallel to it, without interferance so that they are fixed in this position. Having located the pistons 10, as proximally as possible in this zone by means of the nuts 4, the bone is transfixed with the wires 6 through the drilled holes 16 in the pistons 10 on its distal part; thus they are fixed in this position and the correspondent corticotomy is carried out. At in this point the elongation process begins while manipulating the fitting nuts 4 in the pistons 10.

The combined high quality, technical efficiency, and cost effectiveness of the present invention make it an improvement over the prior art in the field.

I claim:

1. An orthopedic external fixation device for positioning fragments of a bone, comprising, structural means for positioning the bone, said structural means having a plane of symmetry at which the bone is generally positioned, said structural means including two spaced, generally parallel bars each including a solid section and a tubular section having an outer surface forming threads, said solid and said tubular sections having a plurality of spaced first and second holes, respectively, a pair of pistons connected to said solid sections slidably mounted in said tubular sections, said pistons having a plurality of spaced third holes capable of being aligned with said second holes, a plurality of spaced transfixing pins extending through the bone and positioned in said first, second, and third holes aligned in a plane normal to said plane of symmetry, nut means threadably mounted to said threads of said tubular sections for locking said transfixing pins extending through said second holes, and stop means for preventing transverse movement of said pins through the bone fragments and the first, second, and third holes.

2. The orthopaedic fixation device according to claim 1, wherein said structural means further includes a pair of generally semicircular, spaced members, one of said members being connected to said two bars at said solid and the other of said members being connected to said tube at said tubular sections; and a pair of spaced rods generally parallel and adjustably connected to said members.

3. The orthopaedic fixation device according to claim 2, further including a bone pin carrier member coupled to each of said said tubular sections, said carrier member further having additional holes adapted to receive additional transfixing pins in another plane generally parallel to said semicircular, spaced members; stop means for preventing transverse movement of said additional pins.

4. The orthopaedic fixation device according to claim 6 wherein said bone pin carrier member is T-shaped.

* * * * *